US012109018B2

(12) United States Patent
Johnson et al.

(10) Patent No.: US 12,109,018 B2
(45) Date of Patent: Oct. 8, 2024

(54) DUAL CAMERA PATIENT MONITORING SYSTEM

(71) Applicant: CareView Communications, Inc., Lewisville, TX (US)

(72) Inventors: Steven Gail Johnson, Highland Village, TX (US); Derek del Carpio, Corinth, TX (US); Jeffrey C. Lightcap, Charleston, SC (US)

(73) Assignee: CareView Communications, Inc., Lewisville, TX (US)

( * ) Notice: Subject to any disclaimer, the term of this patent is extended or adjusted under 35 U.S.C. 154(b) by 238 days.

(21) Appl. No.: 17/194,666

(22) Filed: Mar. 8, 2021

(65) Prior Publication Data

US 2022/0280075 A1    Sep. 8, 2022

(51) Int. Cl.
| | |
|---|---|
| *H04N 23/00* | (2023.01) |
| *A61B 5/11* | (2006.01) |
| *G06V 20/54* | (2022.01) |
| *H04N 23/611* | (2023.01) |
| *H04N 23/62* | (2023.01) |

(52) U.S. Cl.
CPC .......... *A61B 5/1128* (2013.01); *A61B 5/1117* (2013.01); *G06V 20/54* (2022.01); *H04N 23/611* (2023.01); *H04N 23/62* (2023.01); *A61B 2560/0223* (2013.01); *G06V 2201/03* (2022.01)

(58) Field of Classification Search
CPC ................ A61B 5/1128; A61B 5/1117; A61B 2560/0223; A61B 5/0077; G06V 20/54; G06V 2201/03; G06V 10/25; G06V 20/52; G06V 40/16; H04N 5/23216; H04N 5/23219; G16H 40/40
See application file for complete search history.

(56) References Cited

U.S. PATENT DOCUMENTS

| | | | | |
|---|---|---|---|---|
| 4,241,456 | A | * 12/1980 | Nakagaki | ............... G08C 23/04 |
| | | | | 398/208 |
| 2002/0034067 | A1 | * 3/2002 | Massaro | ................. G06F 3/147 |
| | | | | 361/728 |

(Continued)

*Primary Examiner* — Frank F Huang
(74) *Attorney, Agent, or Firm* — Meister Seelig & Fein PLLC

(57) ABSTRACT

A method and system for calibrating cameras of a monitoring system, the method comprises receiving a plurality of video frames including a wide area view of a patient area from a primary camera of a monitoring subsystem and a view of a region of interest within the patient area from a secondary camera of the monitoring subsystem, detecting a patient event based on an analysis of given ones of the plurality of video frames corresponding to the wide area view, transmitting the given ones of the plurality of video frames and an identification of the patient event to a viewer client device, generating detection-based calibration instructions based on the patient event, wherein the detection-based calibration instructions including control information that controls operation of the secondary camera based on a location of the patient event, and transmitting the detection-based calibration instructions to the monitoring subsystem, wherein the monitoring subsystem configures the secondary camera based on the control information of the detection-based calibration instructions.

20 Claims, 8 Drawing Sheets

(56) References Cited

U.S. PATENT DOCUMENTS

| | | | | |
|---|---|---|---|---|
| 2003/0136832 A1* | 7/2003 | Massaro | ............... | A47F 5/0068 |
| | | | | 235/383 |
| 2004/0195774 A1* | 10/2004 | Segan | ................... | G04B 47/048 |
| | | | | 273/359 |
| 2006/0082642 A1* | 4/2006 | Wang | ..................... | H04N 7/142 |
| | | | | 348/14.05 |
| 2007/0049159 A1* | 3/2007 | Kulis, II | ................ | A63H 17/28 |
| | | | | 446/438 |
| 2007/0078566 A1* | 4/2007 | Wang | ..................... | A61B 34/70 |
| | | | | 700/259 |
| 2007/0103890 A1* | 5/2007 | Morehead | ............ | A01K 27/006 |
| | | | | 362/103 |
| 2007/0228755 A1* | 10/2007 | Alvarado | ............... | B62D 41/00 |
| | | | | 340/425.5 |
| 2007/0291128 A1* | 12/2007 | Wang | ..................... | H04N 7/185 |
| | | | | 901/1 |
| 2009/0125147 A1* | 5/2009 | Wang | .................... | G06T 7/0012 |
| | | | | 715/764 |
| 2010/0010672 A1* | 1/2010 | Wang | ...................... | B25J 13/06 |
| | | | | 901/1 |

\* cited by examiner

DUAL CAMERA PATIENT MONITORING SYSTEM

COPYRIGHT NOTICE

A portion of the disclosure of this patent document contains material, which is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

BACKGROUND OF THE INVENTION

Field of the Invention

This application generally relates to a video patient monitoring, and in particular, a system and method utilizing two or more cameras that work in unison to capture separate views or perspectives of a patient subject.

Description of the Related Art

Monitoring systems using cameras are conventionally and generally known. For example, healthcare facilities rely on patient monitoring systems to supplement interventions and reduce the instances of patient falls. Constant eyes-on monitoring of patients can be difficult for healthcare professionals to maintain especially in times of personnel shortage and increased workloads. Various systems and methods for patient video monitoring have been disclosed, such as U.S. Pat. No. 9,311,540 entitled "SYSTEM AND METHOD FOR PREDICTING PATIENT FALLS," U.S. Pat. No. 8,471,899 entitled "SYSTEM AND METHOD FOR DOCUMENTING PATIENT PROCEDURES," U.S. Pat. No. 8,675,059 entitled "SYSTEM AND METHOD FOR USING A VIDEO MONITORING SYSTEM TO PREVENT AND MANAGE DECUBITUS ULCERS IN PATIENTS," and U.S. Pat. No. 9,866,797 entitled "SYSTEM AND METHOD FOR MONITORING A FALL STATE OF A PATIENT AND MINIMIZING FALSE ALARMS." Video monitoring can be used to automate patient monitoring and increase the ability of a healthcare professional to effectively monitor a group of patients distributed between different rooms.

In current patient monitoring systems, a video camera may capture a view of a patient which is used to send a video feed to sitters and analyze for patient motion which suggests a possible fall. An alert can be issued to summon a healthcare professional to intervene when such an event is detected. However, current patient monitoring systems lack remote intervention functionally, such as, basic diagnostics and other telemedicine features that can determine the well-being of a patient which helps alleviate the need for personnel to attend to a patient for non-fall events. There is thus a need for systems and methods that can remotely detect and monitor the status of a patient within a patient area to assist healthcare professionals in reducing unnecessary interventions when events are detected.

SUMMARY OF THE INVENTION

The present invention provides a method, system, and non-transitory computer readable media for calibrating cameras of a monitoring system. According to one embodiment, the method comprises receiving a plurality of video frames including a wide area view of a patient area from a primary camera of a monitoring subsystem and a view of a region of interest within the patient area from a secondary camera of the monitoring subsystem, detecting a patient event based on an analysis of given ones of the plurality of video frames corresponding to the wide area view, transmitting the given ones of the plurality of video frames and an identification of the patient event to a viewer client device, generating detection-based calibration instructions based on the patient event, wherein the detection-based calibration instructions include control information that controls operation of the secondary camera based on a location of the patient event, and transmitting the detection-based calibration instructions to the monitoring subsystem, wherein the monitoring subsystem configures the secondary camera based on the control information of the detection-based calibration instructions.

The control information may include at least one of move, pan, tilt, zoom, focus, lighting, and exposure control. In another embodiment, the control information may include control of the secondary camera to focus or zoom in on an area of interest based on the location of the patient event. The method may further comprise receiving manual calibration instructions from a user of a viewer client device, the manual calibration instructions including control information that manually controls operation of the primary camera or the secondary camera by the user and transmitting the manual calibration instructions to the monitoring subsystem, wherein the monitoring subsystem configures the primary camera or the secondary camera based on the control information of the manual calibration instructions.

The patient event may include at least one of a patient at risk of falling, the patient falling, the patient in need of intervention, the patient outside of a designated area, and patient motion. In one embodiment, detecting the patient event may further comprise detecting the patient event based on a primary field of view of the patient area. Alternatively, detecting the patient event may further comprise detecting the patient event based on a secondary field of view of the patient area. The region of interest may include at least one of a wound, an intravenous insertion, or a face.

According to one embodiment, the system comprises a processor and a memory having executable instructions stored thereon that when executed by the processor cause the processor to receive a plurality of video frames including a wide area view of a patient area from a primary camera of a monitoring subsystem and a view of a region of interest within the patient area from a secondary camera of the monitoring subsystem; detect a patient event based on an analysis of given ones of the plurality of video frames corresponding to the wide area view, transmit the given ones of the plurality of video frames and an identification of the patient event to a viewer client device, generate detection-based calibration instructions based on the patient event wherein the detection-based calibration instructions include control information that controls operation of the secondary camera based on a location of the patient event, and transmit the detection-based calibration instructions to the monitoring subsystem wherein the monitoring subsystem configures the secondary camera based on the control information of the detection-based calibration instructions.

The control information may include at least one of move, pan, tilt, zoom, focus, lighting, and exposure control. The control information may also include control of the secondary camera to focus or zoom in on an area of interest based on the location of the patient event. In one embodiment, the processor may be further configured to receive manual calibration instructions from a user of a viewer client device wherein the manual calibration instructions include control information that manually controls operation of the primary camera or the secondary camera by the user, and transmit the manual calibration instructions to the monitoring subsystem wherein the monitoring subsystem configures the primary camera or the secondary camera based on the control information of the manual calibration instructions.

The patient event may include at least one of a patient at risk of falling, the patient falling, the patient in need of intervention, the patient outside of a designated area, and patient motion. The processor may also be configured to detect the patient event based on a primary field of view of the patient area. In another embodiment, the processor may be configured to detect the patient event based on a secondary field of view of the patient area. The region of interest may include at least one of a wound, an intravenous insertion, or a face.

According to one embodiment, the non-transitory computer-readable media comprises computer program code for receiving a plurality of video frames including a wide area view of a patient area from a primary camera of a monitoring subsystem and a view of a region of interest within the patient area from a secondary camera of the monitoring subsystem, computer program code for detecting a patient event based on an analysis of given ones of the plurality of video frames corresponding to the wide area view, computer program code for transmitting the given ones of the plurality of video frames and an identification of the patient event to a viewer client device, computer program code for generating detection-based calibration instructions based on the patient event wherein the detection-based calibration instructions include control information that controls operation of the secondary camera based on a location of the patient event, and computer program code for transmitting the detection-based calibration instructions to the monitoring subsystem wherein the monitoring subsystem configures the secondary camera based on the control information of the detection-based calibration instructions.

The control information may include at least one of move, pan, tilt, zoom, focus, lighting, and exposure control. The control information may also include control of the secondary camera to focus or zoom in on an area of interest based on the location of the patient event. The patient event may include at least one of a patient at risk of falling, the patient falling, the patient in need of intervention, the patient outside of a designated area, and patient motion.

BRIEF DESCRIPTION OF THE DRAWINGS

The invention is illustrated in the figures of the accompanying drawings which are meant to be exemplary and not limiting, in which like references are intended to refer to like or corresponding parts.

DETAILED DESCRIPTION OF THE INVENTION

Subject matter will now be described more fully hereinafter with reference to the accompanying drawings, which form a part hereof, and which show, by way of illustration, exemplary embodiments in which the invention may be practiced. Subject matter may, however, be embodied in a variety of different forms and, therefore, covered or claimed subject matter is intended to be construed as not being limited to any example embodiments set forth herein; example embodiments are provided merely to be illustrative. It is to be understood that other embodiments may be utilized and structural changes may be made without departing from the scope of the present invention. Likewise, a reasonably broad scope for claimed or covered subject matter is intended. Throughout the specification and claims, terms may have nuanced meanings suggested or implied in context beyond an explicitly stated meaning. Likewise, the phrase "in one embodiment" as used herein does not necessarily refer to the same embodiment and the phrase "in another embodiment" as used herein does not necessarily refer to a different embodiment. It is intended, for example, that claimed subject matter include combinations of exemplary embodiments in whole or in part. Among other things, for example, subject matter may be embodied as methods, devices, components, or systems. Accordingly, embodiments may, for example, take the form of hardware, software, firmware or any combination thereof (other than software per se). The following detailed description is, therefore, not intended to be taken in a limiting sense.

Embodiments of the present invention include systems and methods for monitoring a patient area and detecting patient events therewith. The patient events may include incidents in which a patient is at increased risk of injury or otherwise is in need of intervention. An illustrative system includes a first camera and a second camera. The first camera may have a first field of view and the second camera may have a second field of view that is different than the first field of view.

Figure 1:
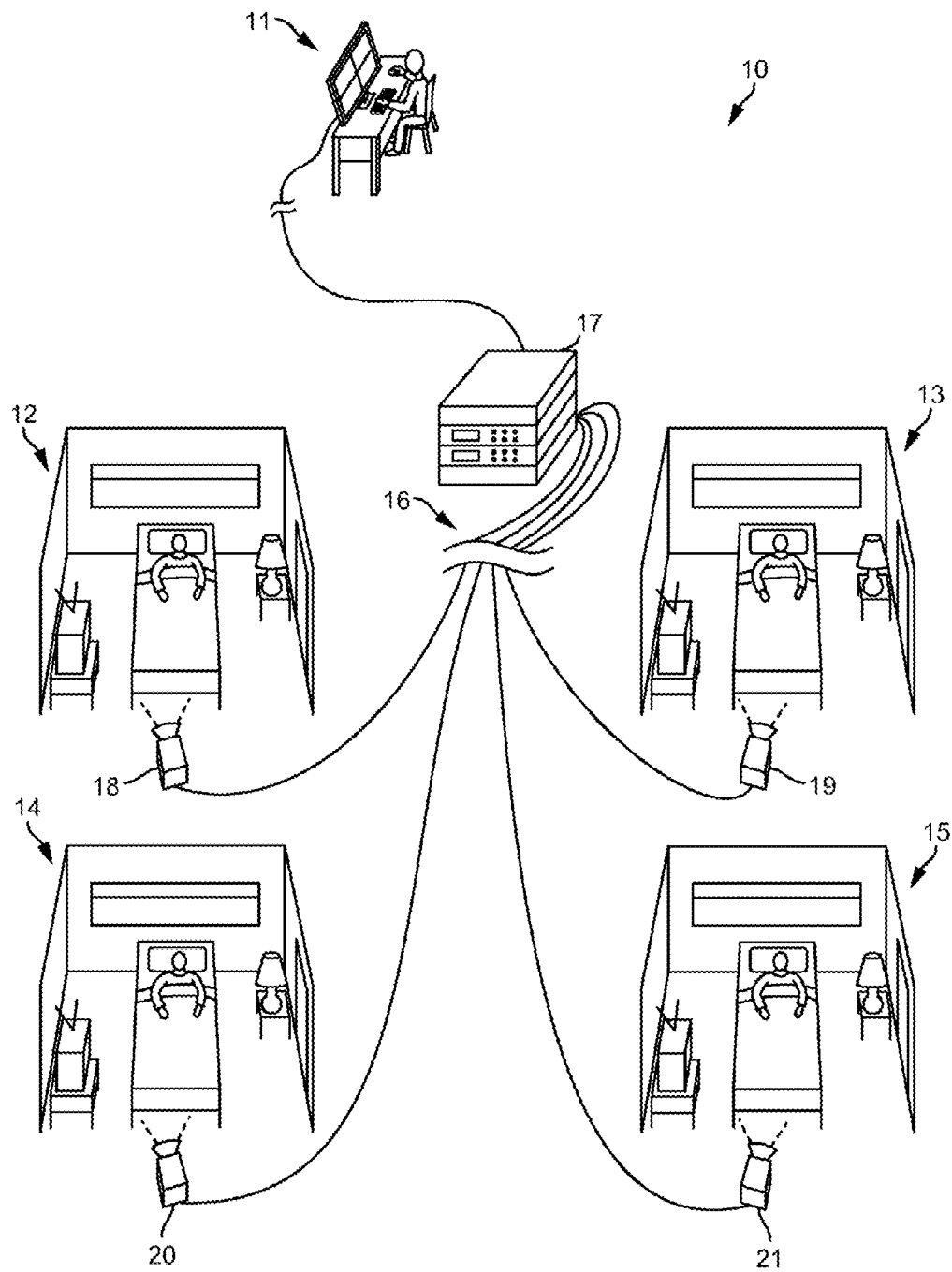
FIG. 1 illustrates a schematic illustration of a monitoring system according to an embodiment of the present invention.

FIG. 1 is a schematic diagram of a patient monitoring system 10. The patient monitoring system 10 can allow a healthcare professional to monitor multiple patient areas 12-15 from a monitoring station 11 via a computing system 17. The monitoring station 11 comprises a user interface, which can include a screen and an input. The screen can display images of the patient areas 12-15, indications of one or more states of the patients being monitored, patient data, and/or other information. In some embodiments, the components of the monitoring station 11 are portable such that the monitoring station 11 can move with the healthcare professional.

While four patient areas 12-15 are shown in FIG. 1, any number of patient areas can be monitored at the monitoring station 11 via the computing system 17. The monitoring station 11 can be remote from the patient areas 12-15. For example, the monitoring station 11 can be on the same or different floor as the patient areas 12-15, in the same or different building as the patient areas 12-15, or located in a geographically different location as the patient areas 12-15.

Furthermore, the patient areas 12-15 can be remote from each other. The computing system 17 can be in one particular location or the components of the computing system 17 can be distributed amongst multiple locations. The computing system 17 can be at the monitoring station 11 or can be remote from the monitoring station 11 and/or the patient areas 12-15.

As shown in FIG. 1, a plurality of cameras 18-21 can be respectively positioned to view and generate frames of the plurality of patient areas 12-15. Information concerning the frames, such as three dimensional pixel information, can be transmitted from the plurality of cameras 18-21 along data channels 16 to the computing system 17. In some cases, the computing system 17 is a single unit, such as a server or a personal computer (e.g., a desktop computer or a laptop computer). In some cases, the computing system 17 is distributed amongst several units, such as one or more personal computers, one or more servers, circuitry within one or more of the cameras 18-21, and/or other computing devices. In some cases, the computing system 17 is part of a cloud computing network. The data channels 16 can be wired lines of a network (e.g., a local area network) and/or wireless channels (e.g., Wi-Fi or cellular network).

Each of the plurality of cameras 18-21 can generate a chronological series of frames (e.g., as images). The plurality of cameras 18-21 can be configured to collect three dimensional information to generate representations of the patient areas 12-15 in three dimensional space. The term camera, as used herein, refers to any device or system of devices configured to optically collect dimensional information. A camera can include one or more sensors configured to register the reception of light in the visible spectrum and/or non-visible spectrum (e.g., along the infrared band). A camera can be a video camera. A camera can comprise one or more laser emitters and one or more laser receivers. In some embodiments, a camera can capture a sequence of frames at a predetermined frame rate, such as six, eight, sixteen, twenty-four, or some other number of frames per second. In some embodiments, a camera can provide infrared illumination or night vision capabilities for operating in low light conditions.

Various camera devices and techniques can be employed to perform a scan of a patient area to collect three dimensional information. Stereoscopic systems and techniques can include the use of two or more cameras viewing the same general area but from different perspectives (e.g., the cameras can be located at different positions). For example, the two cameras may be laterally offset by a few inches. Frames can be simultaneously collected by the cameras and common points between the collected frames can be matched. The frames can then be analyzed to determine which aspects of the two frames are similar to each other and which aspects are not similar to each other. The coordinates of the matching and dissimilar aspects can be determined geometrically (e.g., through triangulation) based on the known offset between the two or more cameras.

A laser based camera system can be used for performing three dimensional scans of a patient area. Such laser based system can have at least one laser and at least one sensor sensitive to reflections of the laser beam. The laser can rapidly scan a laser beam over a scene (e.g., by moving the laser emitter or by moving a mirror, the laser pulsing at discrete points according to a grid) and the sensor can sense reflections of the laser beam reflecting from various features in the scene. The particular direction at which the laser is projected at each moment, and whether an associated reflection was sensed, as well as the time of flight of the laser beam, can be used to build a three dimensional frame of the scene. The time of flight can be calculated from the known time the laser beam was projected and the known time that it was received by the sensor.

Some systems for performing three dimensional scans can include at least one emitter (e.g., laser or infrared based, among other options) and at least one sensor offset from the at least one emitter. Each sensor can be sensitive to the angle at which a reflection of a beam or other projection from the emitter is received after reflecting off of a feature of the scene. The emitter can rapidly scan a scene while the direction and angle of the projection is known at each instance. The angle of reception sensed by the sensor, as well as time of flight, can be determined and the three dimensional coordinates of the reflecting features in the scene can be determined by triangulation or other geometric technique. It is noted that various other techniques for performing three dimensional scans are possible and are contemplated as within the scope of the present disclosure. Various techniques for three dimensional data collection are disclosed in U.S. Patent Application No. 2010/0290698 to Freedman et al., the entirety of which is incorporated herein by reference. While various systems for collecting information in three dimensions are disclosed, embodiments of the present disclosure can be practiced with systems that collect one dimensional information (e.g., a point source sensor) and/or two dimensional information (e.g., a video camera measuring color and light intensity).

Figure 2:
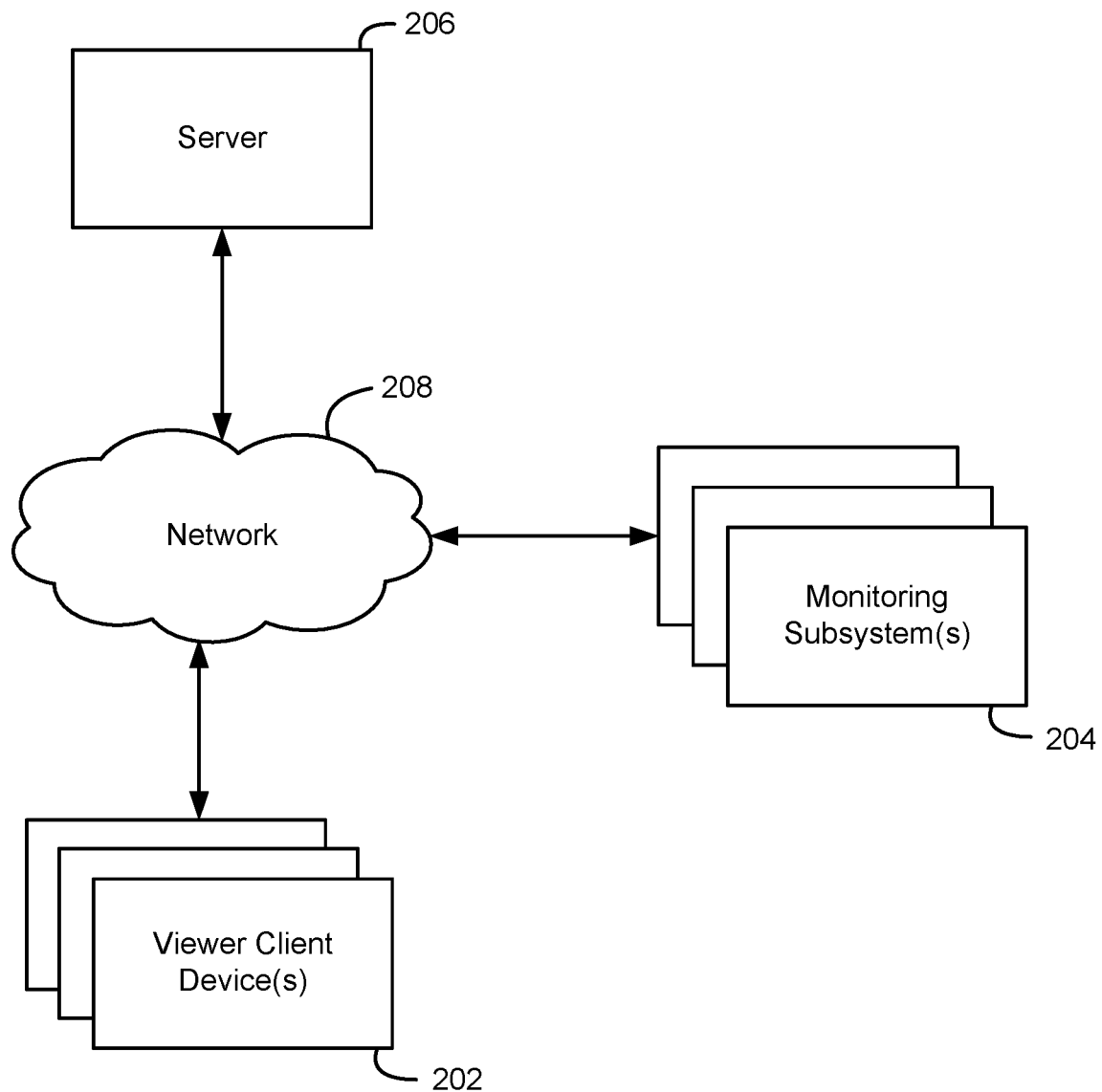
FIG. 2 illustrates a computing system according to an embodiment of the present invention.

FIG. 2 presents a computing system according to an embodiment of the present invention. The computing system comprises viewer client device(s) 202, monitoring subsystem(s) 204, and server 206. Viewer client device(s) 202 can be configured to provide functionality of a monitoring station. Viewer client device(s) 202 may comprise computing devices (e.g., desktop computers, television devices, terminals, laptops, personal digital assistants (PDA), cellular phones, smartphones, tablet computers, e-book readers, smart watches and smart wearable devices) including at least a central processing unit and memory capable of connecting to a network. The memory can be one or more discrete non-transient computer readable storage medium components (e.g., RAM, ROM, NVRAM, EEPROM, and/or FLASH memory) for storing program instructions and/or data. The processor can be configured to execute program instructions stored on the memory to control the viewer client device(s) 202 in carrying out the methods disclosed herein. The viewer client device(s) 202 can include a network controller for facilitating communication with monitoring subsystem(s) 204 and/or other remote components.

Viewer client device(s) 202 may also include display circuitry, such as, graphics processor and graphics memory which can provide a graphics output to a screen and support user interface functionality (e.g., a graphical user interface (GUI) or a browser application provided on a display). The display circuitry may be part of a separate display, such as a screen, handheld device, or remote terminal. The display circuitry can facilitate the display of frames taken by cameras from monitoring subsystem(s) 204, view alerts from monitoring subsystem(s) 204, establish a communication connection with a patient via monitoring subsystem(s) 204, and activate a distress or call nurse functionality to signal for assistance. The viewer client device(s) 202 may also include user input circuitry for accepting user commands, such as, a keyboard, mouse, trackball, touchpad, touch screen, joystick, slider bar, or any other control. The user input circuitry can facilitate the definition of boundaries and monitoring zones, as will be further described herein.

The viewer client device(s) 202 may also include or execute an application to communicate content, such as, for example, textual content, multimedia content, or the like. A viewer client device may also include or execute an application to perform a variety of possible tasks, such as browsing, searching, playing various forms of content, including locally stored or streamed video. Viewer client device(s) 202 may include or execute a variety of operating systems, including a personal computer operating system, such as a Windows, Mac OS or Linux, or a mobile operating system, such as iOS, Android, or Windows Phone, or the like. A viewer client device may include or may execute a variety of possible applications, such as a client software application enabling communication with other devices, such as communicating one or more messages, such as via email, short message service (SMS), or multimedia message service (MMS).

Each of monitoring subsystem(s) 204 may include a plurality of cameras and/or sensors where each of which may capture a variety of views simultaneously. A camera may include an emitter that can emit light or electromagnetic radiation. In various embodiments, the emitter can emit visible light, non-visible light, laser light, and any other type of light. Some camera embodiments may not include an emitter and may use, for example, ambient light. In some embodiments, the light, whether emitted by an emitter or ambient, can reflect off of features of a scene and be received by a sensor that can convert the light into electronic signals. The sensor can include a charge-coupled device (CCD) or a complementary metal-oxide-semiconductor (CMOS), among other options. A camera may also include optics for directing and/or receiving light. The optics can include a mirror (e.g., for reflecting a laser), a lens, a filter, and/or other components for sending, capturing, and/or conditioning light. The camera can include a motor for moving one or more components of the camera. For example, the motor may be used to scan light over a scene by moving an emitter or a mirror.

A camera may further include a processor and memory. The processor can perform various computing functions, such as those described herein or otherwise useful for operating the camera. The memory can be a non-transient computer readable storage medium (e.g., random access memory or flash) for storing program instructions and/or frames. For example, a camera's processor can be configured to execute program instructions stored on the memory for controlling the camera in scanning a scene with emitted light and converting reflected light into digital signals with a sensor, storing the digital signals on the memory as three dimensional frame data, transferring the frame data to server 206, and/or performing any other function. The processor may perform various signal conditioning and/or image processing on the frames. The processor may include a dedicated video processor for image processing.

Server 206 may comprise at least a special-purpose digital computing device including at least one or more central processing units and memory. The server 206 may also include one or more of mass storage devices, power supplies, wired or wireless network interfaces, input/output interfaces, and operating systems, such as Windows Server, Mac OS X, Unix, Linux, FreeBSD, or the like. In an example embodiment, the server may include or have access to memory or computer readable storage devices for storing instructions or applications for the performance of various functions and a corresponding processor for executing stored instructions or applications. For example, the memory may store an instance of the server 206 configured to operate in accordance with the disclosed embodiments.

In certain embodiments, server 206 may comprise cloud server(s) that facilitate provisioned resources and services to viewer client device(s) 202. Cloud server(s) may comprise a system that abstracts the use of shared resources to provide services to viewer client device(s) 202 through network 208. Server 206 may also provide on-demand access to a shared pool of configurable computing resources (not illustrated) such as computer networks, servers, applications and services, etc. Furthermore, server 206 may be configured to provide services with a storage system through the implementation of a software as a service ('SaaS') service model where the server 206 may offer application software, databases, as well as the platforms that may be used to run applications on the storage system to provide on-demand software and eliminating the need to install and run the application on local computers.

Server 206 may include a video storage and retrieval device for receiving video or image frame data from monitoring subsystem(s) 204 and storing said data. In one embodiment, the video or image frame data may be stored permanently, or, alternatively, may be stored temporarily solely for processing. Video data may be stored in a number of formats and on a number of mechanisms such as flat file storage, relational database storage, or the like. Server 206 is further operable to receive video data from the video storage and retrieval device and monitor the video data to detect patient events by analyzing incoming video or image frames using techniques such as machine learning. Analyzing the video or image frames may include extracting features from the video or image frames and executing a supervised learning process to classify a given frame as containing a patient event or not. A patient event can include patient changes, such as in a patient's position or condition, patient gestures, conditions where a patient is at risk of falling, a patient falling (e.g., while leaving a bed), a patient in need of intervention, a patient outside of a designated area, and patient motion, among various other events.

Exemplary techniques that may be used to detect patient events include virtual bedrails (described in further detail in commonly owned U.S. Pat. No. 9,311,540 entitled "SYSTEM AND METHOD FOR PREDICTING PATIENT FALLS" which is herein incorporated by reference in its entirety), thermal detection (described in further detail in commonly owned U.S. Pat. No. 9,959,471 entitled "PATIENT VIDEO MONITORING SYSTEMS AND METHODS FOR THERMAL DETECTION OF LIQUIDS" which is herein incorporated by reference in its entirety), motion feature patterns (described in further detail in commonly owned U.S. Pat. No. 10,055,961 entitled "SURVEILLANCE SYSTEM AND METHOD FOR PREDICTING PATIENT FALLS USING MOTION FEATURE PATTERNS" which is herein incorporated by reference in its entirety), and patient support surface zones (described in further detail in commonly owned U.S. Pat. No. 9,866,797 entitled "SYSTEM AND METHOD FOR MONITORING A FALL STATE OF A PATIENT AND MINIMIZING FALSE ALARMS" which is herein incorporated by reference in its entirety).

After classifying a given frame, the server 206 may then transmit the results of the classification along with a corresponding stream of video or image frames including the given frame to the viewer client device(s) 202. Alternatively, the stream of video or image frames may be transmitted to the viewer client device(s) 202 without classification. Additionally, server 206 may transmit calibration information to monitoring subsystem(s) 204 to reposition or focus one or more cameras based on specific detected events by server 206 or in response to a manual instruction from viewer client device(s) 202. For example, changes in a patient's position or condition detected by server 206 using video from a primary camera may trigger moving or refocusing of a secondary camera. Alternatively, viewer client device(s) 202 may transmit instructions to server 206 for focusing on a specific region of a patient which requires more specific monitoring or for focusing on the patient's face when communicating with the patient.

Network 208 may be any suitable type of network allowing transport of data communications across thereof. The network 208 may couple devices so that communications may be exchanged, such as between server 206, viewer client device(s) 202, and monitoring subsystem(s) 204 or other types of devices. The network 208 may also include mass storage, such as network attached storage (NAS), a storage area network (SAN), cloud computing and storage, or other forms of computer or machine-readable media, for example. In one embodiment, the network 208 may be the Internet, following known Internet protocols for data communication, or any other communication network, e.g., any local area network (LAN) or wide area network (WAN) connection, cellular network, wire-line type connections, wireless type connections, or any combination thereof.

Figure 3:
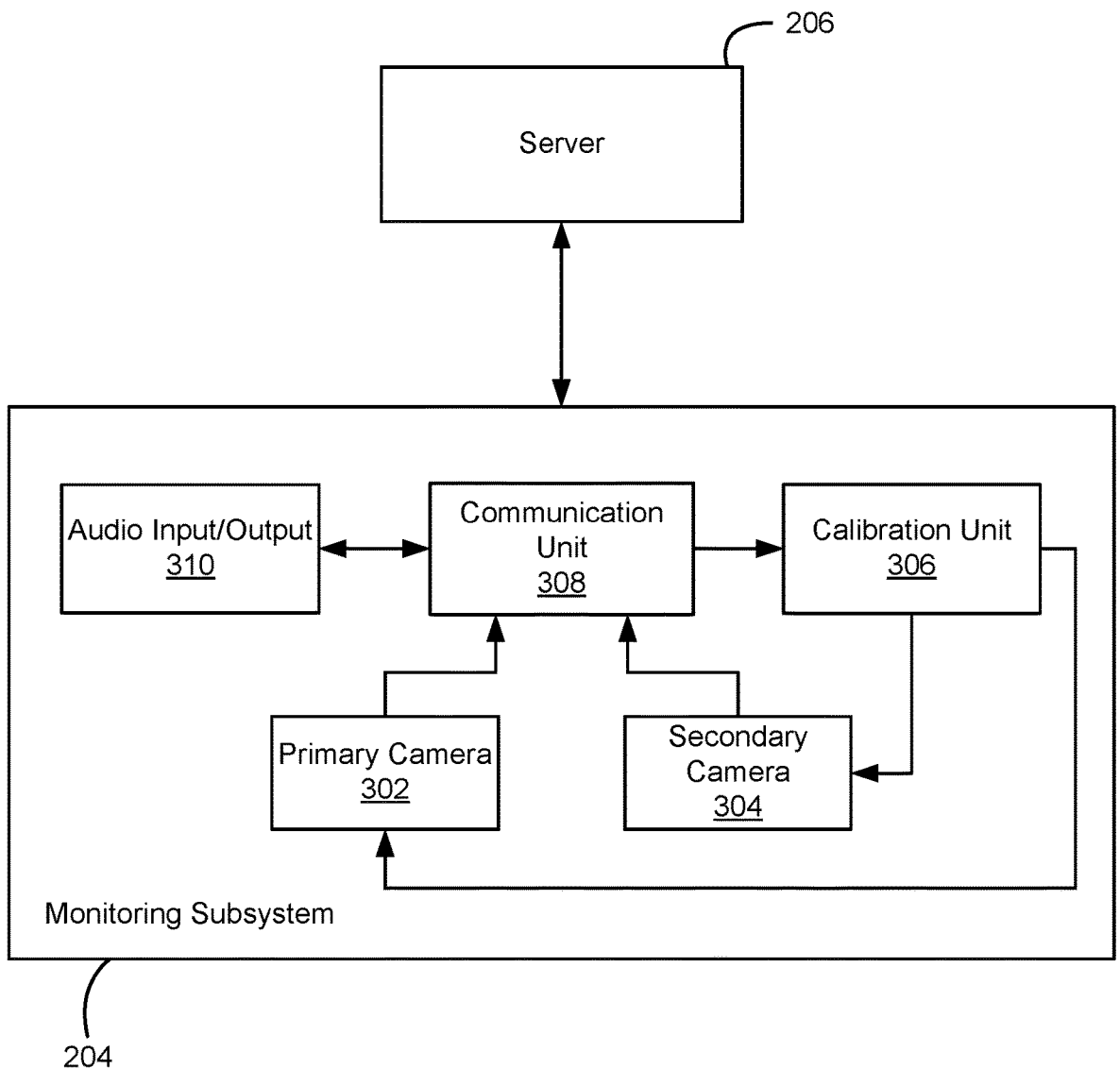
FIG. 3 illustrates a block diagram of components of a monitoring system according to an embodiment of the present invention.

FIG. 3 presents a block diagram of components of a monitoring system according to an embodiment of the present invention. Monitoring subsystem 204 includes a primary camera 302 and a secondary camera 304. Primary camera 302 and secondary camera 304 may be placed adjacent to each other and configured to monitor a given patient area. The primary camera 302 and secondary camera 304 may comprise visible light cameras and/or special-purpose cameras, such as a thermal image camera, an infrared camera, a vision camera, a filter camera or the like. The primary camera 302 and/or the secondary camera 304 may also comprise high-definition cameras including, for example, a zoom lens, an imaging section including CCDs, and a driving mechanism for driving and controlling the zoom lens to pan (to move to a prescribed position in a horizontal direction), to tilt (to move to a prescribed position in a vertical direction) and to zoom.

The primary camera 302 may be configured to capture a primary view of a patient. The primary view of the patient may include, for example, a wide area view that captures an entirety of a patient area or monitored zone. The secondary camera 304 may be configured to capture a secondary view of the patient. The secondary view may capture a pointed or focused view of a specific region of the patient which requires more specific monitoring or viewing. For example, the disclosed system can be used to deliver telemedicine where a doctor can use viewer client device(s) 202 to move, tilt, and zoom the secondary camera 304 to look at a desired location (e.g., a wound, an intravenous insertion, or the patient's face) and while talking to the patient with primary camera 302. The primary and secondary views may be viewed simultaneously or switched from one to another at the viewer client device(s) 202.

Monitoring subsystem 204 also includes a communication unit 308 for transferring video data, audio data, and control signals with server 206 via wireless signals or wired lines. Video data and audio data corresponding to the primary and secondary views may be transmitted from monitoring subsystem 204 to server 206 via the communication unit 308 and streamed to viewer client device(s) 202 in real-time (either directly from monitoring subsystem 204 or indirectly through server 206). The monitoring subsystem 204 also includes audio input/output 310 that may be connected to speakers, microphones, and other audio equipment. Audio data may be captured or recorded from a patient area and transmitted to server 206 and/or viewer client device(s) 202, and vice versa where audio from server 206 and/or viewer client device(s) 202 may be outputted to, for example, speakers in a patient area.

Server 206 may further transmit control information to calibration unit 306 that controls operation of primary camera 302 and/or secondary camera 304 (e.g., move, pan, tilt, zoom, focus, lighting, or exposure controls, etc.) based on the control information. The calibration unit 306 may include a computer including, for example, a central processing unit, memory, input/output port, and a camera driving circuit. The control information may be generated from either server 206 or viewer client device(s) 202. For example, if a patient is detected by server 206 to be in motion in a view of the primary camera 302, a trajectory or motion vector may be calculated by server 206 and used to direct the primary camera 302 to turn or move to retain its focus on the area of attention.

As another example, if a user of viewer client device(s) 202 wants to check a patient's temperature due to a detected change in thermal temperature of the patient (as described in further detail in commonly owned U.S. Pat. No. 9,959,471), the viewer client device(s) 202 could direct the secondary camera 304 to focus on the patient's face to detect sweating or switch to a thermal imaging mode and detect a fever/heat. The secondary camera 304 can also be programmed to auto focus or zoom in on an area of interest, such as a wound, face, intravenous location, etc., based on feedback from an analysis received by the server 206 of a view of images from the primary camera 302, or instructions from the viewer client device(s) 202. If a user of viewer client device(s) 202 tries to communicate with the patient because he's moving, server 206 may also automatically locate the patient's face (e.g. using facial recognition) and focus the secondary camera 304 on the patient's face so the user can talk and see their face.

Server 206 may determine an area for display on viewer client device(s) 202 and generate control information that provides, for example, positional control (by pan and tilt driving) and magnification ratio control (by zoom driving) of the primary camera 302 and the secondary camera 304. Server 206 may also analyze videos by performing object detection, object tracking, object type identification, speed detection, etc., and generate control information based on the analysis. In one embodiment, a detected view of primary camera 302 may be used to adjust and control the position and zoom of either or both of the primary camera 302 and the secondary camera 304. In another embodiment, the server 206 may analyze video provided from monitoring subsystem 204 to detect certain events (e.g., patient fall events, thermal events, etc.) and may be used to change functionality of secondary camera 304 based on particular events.

Figure 4:
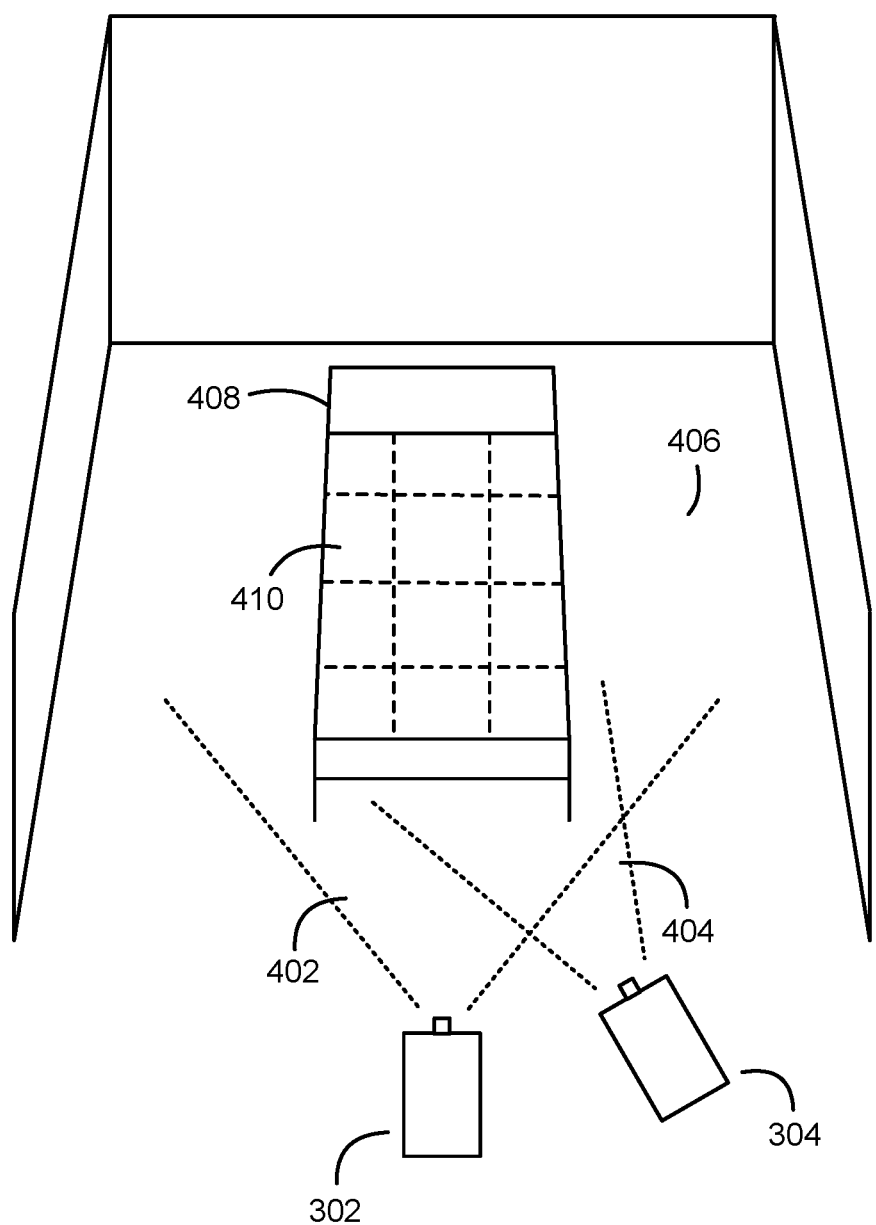
FIG. 4 illustrates exemplary configuration of patient monitoring according to an embodiment of the present invention.

FIG. 4 illustrates exemplary configuration of patient monitoring according to an embodiment of the present invention. Primary camera 302 is configured within a patient area 406 to capture video or a sequence of video frames including a primary field of view 402 while secondary camera 304 is configured within the patient area 406 to capture video or a sequence of video frames including a secondary field of view 404. Primary camera 302 and secondary camera 304 may be configured in any location within patient area 406 and are not limited to the configurations of the illustrated embodiment. Additionally, secondary camera 304 may be configured in relation to primary camera 302 in a variety of configurations. That is, secondary camera 304 may be oriented relative to, adjacent to, or offset from primary camera 302 by any distance or orientation.

Secondary field of view 404 can overlap or include a portion of primary field of view 402. For example, primary field of view 402 may comprise a wide area view of patient area 406. Patient area 406 includes a patient support surface 408. Secondary field of view 404 may comprise a zoomed or focused view of patient area 406, such as a view of patient support surface 408. In one embodiment, secondary camera 304 may have a resolution higher than that of the primary camera 302 and capture video of the patient area 406 (or portions thereof) with the higher resolution. According to another embodiment, secondary field of view 404 may include a zoomed or focused view of patient area 406 that is outside of patient support surface 408, for example, an area adjacent to a side of patient support surface 408, a bedside table, or floor surface.

In yet another embodiment, second field of view 404 may comprise an enlarged or enhanced video of a portion of primary field of view 402 corresponding one or more of monitoring zones 410. Primary field of view 402 may configured to capture video used for monitoring of patient events of a wide area view of patient area 406 while secondary field of view 404 may be configured to focus attention to one or more of monitoring zones 410 based on the monitoring of patient events. Alternatively, secondary field of view 404 may be configured to capture video used for monitoring of the one or more monitoring zones 410, such as enhanced or supplemental monitoring and detection in addition to monitoring of the primary field of view 402. Monitoring zones 410 may comprise a division of a monitored area (e.g., patient support surface 408) into a plurality of identifiable zones. The identifiable zones may be associated with certain body parts or bed portions. For example, lower ones of monitoring zones 410 can represent the lower half, or foot, of patient support surface 408. Upper ones of monitoring zones 410 can represent the upper half, or head, of the patient support surface 408. As such, specific monitoring or detection may be configured for each of monitoring zones 410 corresponding to a different body part or bed portion.

Figure 5A:
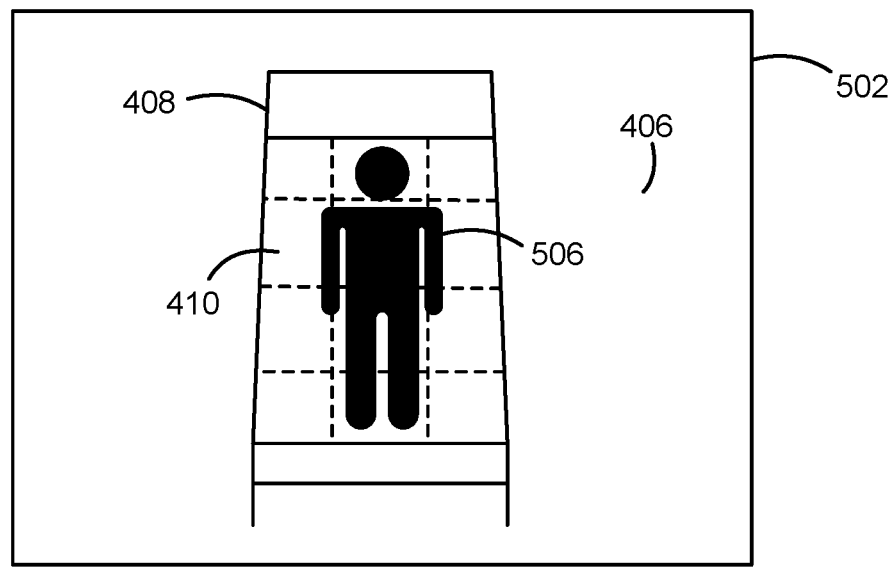
FIGS. 5A, 5B, 5C, 5D, 5E, and 5F illustrate exemplary calibration of camera fields of view according to an embodiment of the present invention.
Figure 5B:
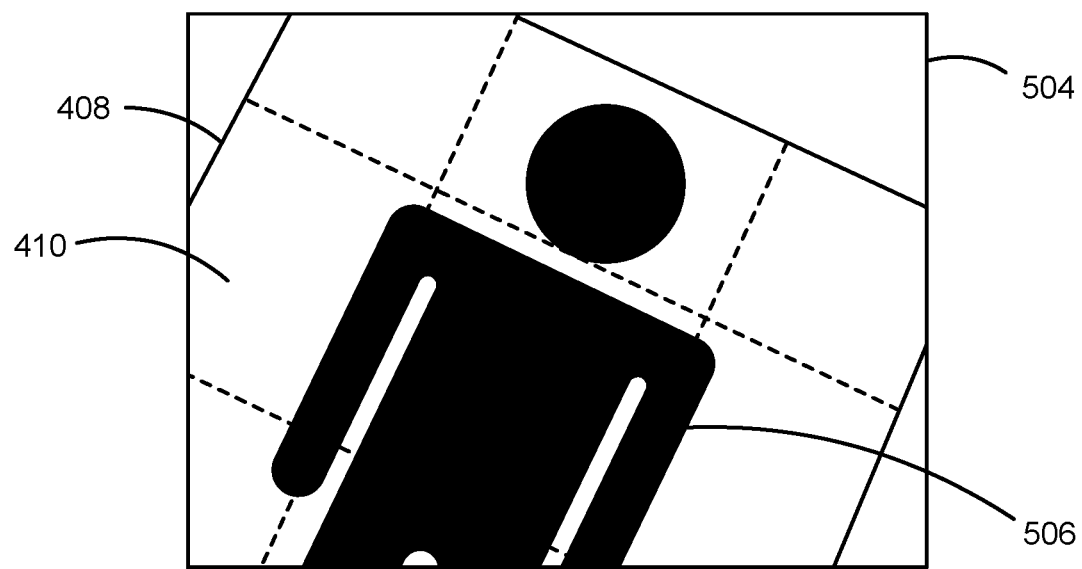

FIGS. 5A through 5F present exemplary calibration of camera fields of view according to an embodiment of the present invention. The embodiment illustrated in FIG. 5A includes a camera view 502 that may be captured by primary camera 302. The camera view 502 comprises a wide area view (e.g., captured within primary field of view 402) of patient 506 on patient support surface 408 in patient area 406. A focused view (e.g., captured within secondary field of view 404) of the patient 506 may be captured by secondary camera 304 in camera view 504 as illustrated in FIG. 5B. The focused view may comprise a region of interest that garners additional attention and is dedicated for capture by secondary camera 304.

Figure 5C:
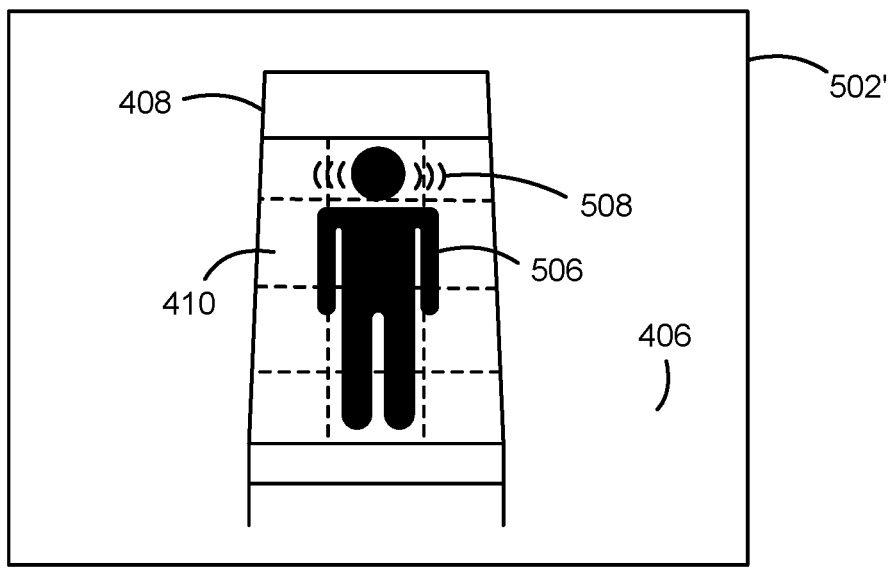
Figure 5D:
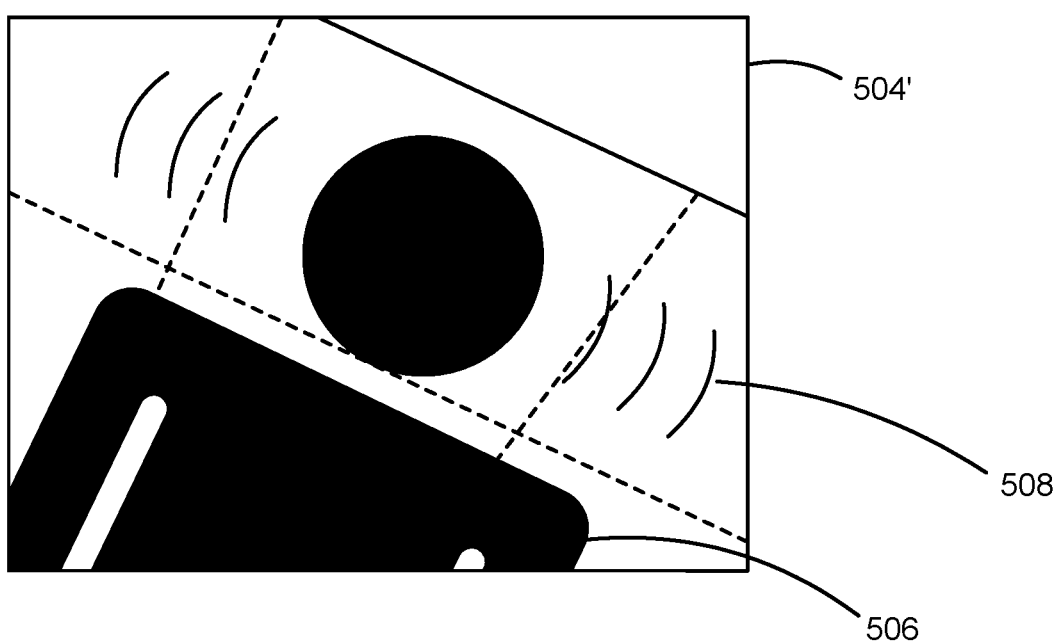
Figure 5E:
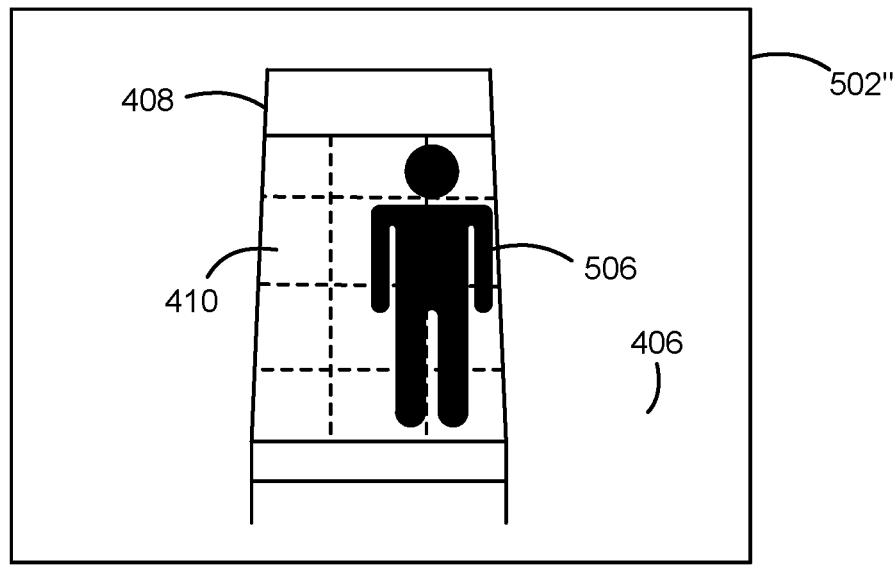
Figure 5F:
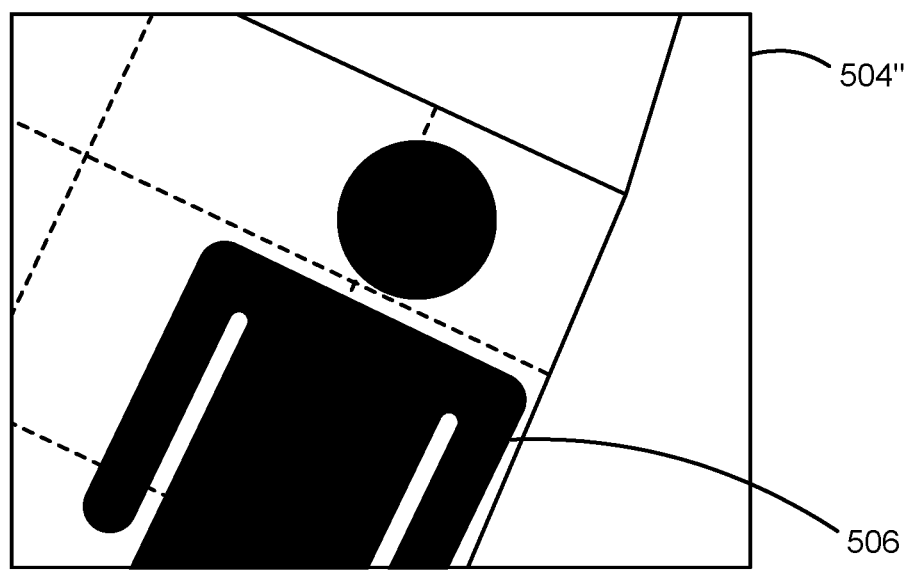

According to embodiments of the present invention, the focused view that is captured by secondary camera 304 may be adjusted or calibrated based on detections of patient events using image frames including the camera view captured by primary camera 302. In one embodiment, camera view 502' comprises a wide area view of patient 506 including patient motion or distress 508, as illustrated in FIG. 5C. Patient motion or distress 508 may comprise a detectable patient event that triggers a calibration (e.g., zoom function) of secondary camera 304 to adjust the focused view to a region of interest corresponding to the location of the patient motion or distress 508 as illustrated by camera view 504' in FIG. 5D. In another embodiment, camera view 502" comprises a wide area view of patient 506 where the patient 506 has moved to a far side of the patient support surface 408, as illustrated in FIG. 5E. The movement of patient 506 may comprise a detectable patient event that triggers a calibration (e.g., pan function) of secondary camera 304 to adjust the focused view of patient 506 to retain a focus on the region of interest corresponding to a location the patient has moved as illustrated by camera view 504" in FIG. 5F.

Figure 6:
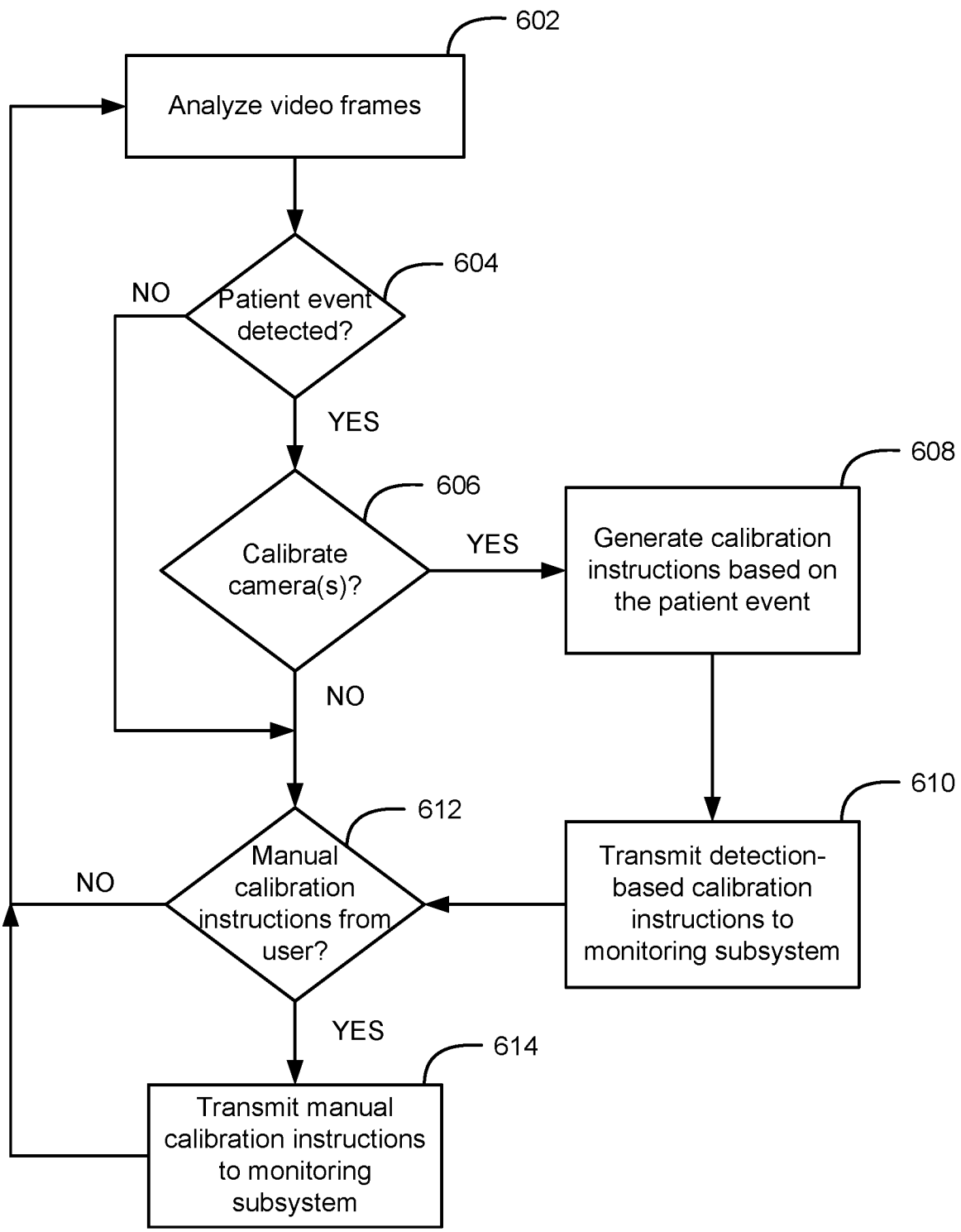
FIG. 6 illustrates a flowchart of a method for calibrating cameras of a monitoring system according to an embodiment of the present invention.

FIG. 6 presents a flowchart of a method for calibrating cameras of a monitoring system according to an embodiment of the present invention. A computing system (e.g., server) may receive surveillance video including a plurality of video frames of a patient area. The frames may be part of a chronological series of frames generated by a camera of a monitoring subsystem and transmitted to the computing system in sequence. Additionally, the plurality of video frames may be received and processed from all cameras of the monitoring subsystem on an individual basis, e.g., from a primary camera and a secondary camera. The plurality of video frames may be further recorded and retrieved from a video storage device.

The plurality of video frames is analyzed, step 602. The plurality of video frames may be analyzed based on monitoring area settings. Monitoring area settings may be configured to define a range of monitoring (e.g., for a primary field of view) and divide the monitoring range into a plurality of monitoring areas (e.g., for a secondary field of view). The analysis may include detecting a patient event that is triggered by the plurality of video frames. A patient event may include a patient at risk of falling, a patient falling (e.g., while leaving a bed), a patient in need of intervention, a patient outside of a designated area, and patient motion, among various other events. The analysis may also detect patient events based on a corresponding field of view. That is, monitoring configured for video frames corresponding to a primary field of view may be distinctive from monitoring configured for video frames corresponding to a secondary field of view.

The computing system determines whether a patient event is detected from the analysis, step 604. Video frames may be labeled to identify whether they include patient events. For example, a fall prediction system may be configured to capture video frames and trigger alerts based on identified motion as described in commonly-owned U.S. Pat. No. 9,041,810. Alternatively, the method may utilize unsupervised clustering techniques to automatically label video. The video frames may be transmitted to a view client device including any identification of detected patient events.

If a patient event is detected, the computing system determines whether the patient event detection triggers a calibration of at least one camera, step 606. Specific patient events may require recalibration of one or more cameras. For example, a secondary camera can be instructed to auto focus or zoom in on a given monitoring area or an area of interest, such as a wound, face, intravenous location, etc., based on patient event detection corresponding to the area of interest. Other patient event detections, however, may not instruct a change in camera calibration.

If a patient event is not detected in step 604, or if camera calibration is not triggered based on the patient event detection in step 606, the method proceeds to determine whether manual calibration instructions are received from a user of the viewer client device, step 612. The manual calibration instructions may include control information that the user may specify to control operation of one or more cameras by the user (e.g., move, pan, tilt, zoom, focus, lighting, exposure, etc. of a primary or secondary camera). For example, a user of the viewer client device can move, tilt, and zoom a secondary camera to look at a desired location for capturing in the video frames (e.g., a wound, an intravenous insertion, or the patient's face) by specifying manual calibration instructions via a user interface on the viewer client device. If manual calibration instructions are received from the user, the manual calibration instructions from the user are transmitted to the monitoring subsystem, step 614, where the monitoring subsystem may configure the primary camera and/or the secondary camera either via a calibration unit, or directly using the control information of the manual calibration instructions from the user, after which the method may proceed to step 602 to analyze additional video frames. Otherwise, the method may directly return to step 602 to analyze additional video frames.

Returning to step 606, if camera calibration is triggered based on the patient event detection, the method proceeds to generate calibration instructions based on the detected patient event, step 608. Generating the detection-based calibration instructions may include determining a location of the detected patient event. As such, the detection-based calibration instructions may include control information that controls operation of one or more cameras (e.g., move, pan, tilt, zoom, focus, lighting, exposure, etc. of a primary or secondary camera) based on or towards the location of the patient event. The detection-based calibration instructions are transmitted to the monitoring subsystem, step 610. The monitoring subsystem may configure the primary camera and/or the secondary camera either via a calibration unit, or directly using the control information of the detection-based calibration instructions. The method may then proceed to step 612 to determine whether manual calibration instructions are also received from the user of the viewer client device. The manual calibration instructions may override the detection-based calibration instructions. If manual calibration instructions are received from the user, then the manual calibration instructions from the user are transmitted to the monitoring subsystem, step 614, and then the method may proceed to step 602. Otherwise, the method may directly return to step 602.

FIGS. 1 through 6 are conceptual illustrations allowing for an explanation of the present invention. Notably, the figures and examples above are not meant to limit the scope of the present invention to a single embodiment, as other embodiments are possible by way of interchange of some or all of the described or illustrated elements. Moreover, where certain elements of the present invention can be partially or fully implemented using known components, only those portions of such known components that are necessary for an understanding of the present invention are described, and detailed descriptions of other portions of such known components are omitted so as not to obscure the invention. In the present specification, an embodiment showing a singular component should not necessarily be limited to other embodiments including a plurality of the same component, and vice-versa, unless explicitly stated otherwise herein. Moreover, applicants do not intend for any term in the specification or claims to be ascribed an uncommon or special meaning unless explicitly set forth as such. Further, the present invention encompasses present and future known equivalents to the known components referred to herein by way of illustration.

It should be understood that various aspects of the embodiments of the present invention could be implemented in hardware, firmware, software, or combinations thereof. In such embodiments, the various components and/or steps would be implemented in hardware, firmware, and/or software to perform the functions of the present invention. That is, the same piece of hardware, firmware, or module of software could perform one or more of the illustrated blocks (e.g., components or steps). In software implementations, computer software (e.g., programs or other instructions) and/or data is stored on a machine-readable medium as part of a computer program product and is loaded into a computer system or other device or machine via a removable storage drive, hard drive, or communications interface. Computer programs (also called computer control logic or computer-readable program code) are stored in a main and/or secondary memory, and executed by one or more processors (controllers, or the like) to cause the one or more processors to perform the functions of the invention as described herein. In this document, the terms "machine readable medium," "computer-readable medium," "computer program medium," and "computer usable medium" are used to generally refer to media such as a random access memory (RAM); a read only memory (ROM); a removable storage unit (e.g., a magnetic or optical disc, flash memory device, or the like); a hard disk; or the like.

The foregoing description of the specific embodiments will so fully reveal the general nature of the invention that others can, by applying knowledge within the skill of the relevant art(s) (including the contents of the documents cited and incorporated by reference herein), readily modify and/or adapt for various applications such specific embodiments, without undue experimentation, without departing from the general concept of the present invention. Such adaptations and modifications are therefore intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one skilled in the relevant art(s).

What is claimed is:

1. A method, in a data processing system comprising a processor and a memory, for calibrating cameras of a monitoring system, the method comprising:
   receiving a plurality of video frames including a wide area view of a patient area from a primary camera of a monitoring subsystem and a view of a region of interest within the patient area from a secondary camera of the monitoring subsystem, the secondary camera comprising visible light and thermal imaging functionality;
   detecting a patient event based on an analysis of given ones of the plurality of video frames corresponding to the wide area view;
   transmitting the given ones of the plurality of video frames and an identification of the patient event to a viewer client device;
   generating detection-based calibration instructions based on the patient event, the detection-based calibration instructions including control information that controls the functionality and operation of the secondary camera based on a location of the patient event; and
   transmitting the detection-based calibration instructions to the monitoring subsystem, wherein the monitoring subsystem configures the functionality and operation of the secondary camera based on the control information of the detection-based calibration instructions.

2. The method of claim 1 wherein the control information includes at least one of move, pan, tilt, zoom, focus, lighting, and exposure control.

3. The method of claim 1 wherein the control information includes control of the secondary camera to focus or zoom in on an area of interest based on the location of the patient event.

4. The method of claim 1 further comprising:
receiving manual calibration instructions from a user of a viewer client device, the manual calibration instructions including control information that manually controls operation of the primary camera or the secondary camera by the user; and
transmitting the manual calibration instructions to the monitoring subsystem, wherein the monitoring subsystem configures the primary camera or the secondary camera based on the control information of the manual calibration instructions.

5. The method of claim 1 wherein the patient event includes at least one of a patient at risk of falling, the patient falling, the patient in need of intervention, the patient outside of a designated area, and patient motion.

6. The method of claim 1 wherein detecting the patient event further comprises detecting the patient event based on a primary field of view of the patient area.

7. The method of claim 1 wherein detecting the patient event further comprises detecting the patient event based on a secondary field of view of the patient area.

8. The method of claim 1 wherein the region of interest includes at least one of a wound, an intravenous insertion, or a face.

9. A system for calibrating cameras of a monitoring system, the system comprising:
a processor; and
a memory having executable instructions stored thereon that when executed by the processor cause the processor to:
receive a plurality of video frames including a wide area view of a patient area from a primary camera of a monitoring subsystem and a view of a region of interest within the patient area from a secondary camera of the monitoring subsystem, the secondary camera comprising visible light and thermal imaging functionality;
detect a patient event based on an analysis of given ones of the plurality of video frames corresponding to the wide area view;
transmit the given ones of the plurality of video frames and an identification of the patient event to a viewer client device;
generate detection-based calibration instructions based on the patient event, the detection-based calibration instructions including control information that controls the functionality and operation of the secondary camera based on a location of the patient event; and
transmit the detection-based calibration instructions to the monitoring subsystem, wherein the monitoring subsystem configures the functionality and operation of the secondary camera based on the control information of the detection-based calibration instructions.

10. The system of claim 9 wherein the control information includes at least one of move, pan, tilt, zoom, focus, lighting, and exposure control.

11. The system of claim 9 wherein the control information includes control of the secondary camera to focus or zoom in on an area of interest based on the location of the patient event.

12. The system of claim 9 further comprising the processor configured to:
receive manual calibration instructions from a user of a viewer client device, the manual calibration instructions including control information that manually controls operation of the primary camera or the secondary camera by the user; and
transmit the manual calibration instructions to the monitoring subsystem, wherein the monitoring subsystem configures the primary camera or the secondary camera based on the control information of the manual calibration instructions.

13. The system of claim 9 wherein the patient event includes at least one of a patient at risk of falling, the patient falling, the patient in need of intervention, the patient outside of a designated area, and patient motion.

14. The system of claim 9 further comprising the processor configured to detect the patient event based on a primary field of view of the patient area.

15. The system of claim 9 further comprising the processor configured to detect the patient event based on a secondary field of view of the patient area.

16. The system of claim 9 wherein the region of interest includes at least one of a wound, an intravenous insertion, or a face.

17. Non-transitory computer-readable media comprising program code that when executed by a programmable processor causes execution of a method for calibrating cameras of a monitoring system, the computer-readable media comprising:
computer program code for receiving a plurality of video frames including a wide area view of a patient area from a primary camera of a monitoring subsystem and a view of a region of interest within the patient area from a secondary camera of the monitoring subsystem, the secondary camera comprising visible light and thermal imaging functionality;
computer program code for detecting a patient event based on an analysis of given ones of the plurality of video frames corresponding to the wide area view;
computer program code for transmitting the given ones of the plurality of video frames and an identification of the patient event to a viewer client device;
computer program code for generating detection-based calibration instructions based on the patient event, the detection-based calibration instructions including control information that controls the functionality and operation of the secondary camera based on a location of the patient event; and
computer program code for transmitting the detection-based calibration instructions to the monitoring subsystem, wherein the monitoring subsystem configures the functionality and operation of the secondary camera based on the control information of the detection-based calibration instructions.

18. The non-transitory computer-readable media of claim 17 wherein the control information includes at least one of move, pan, tilt, zoom, focus, lighting, and exposure control.

19. The non-transitory computer-readable media of claim 17 wherein the control information includes control of the secondary camera to focus or zoom in on an area of interest based on the location of the patient event.

20. The non-transitory computer-readable media of claim 17 wherein the patient event includes at least one of a patient at risk of falling, the patient falling, the patient in need of intervention, the patient outside of a designated area, and patient motion.

* * * * *